(12) United States Patent
Pribanic

(10) Patent No.: US 8,968,191 B2
(45) Date of Patent: Mar. 3, 2015

(54) EXPANDABLE ACCESS ASSEMBLY INCLUDING AN INTERNAL THREAD MECHANISM

(75) Inventor: Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 232 days.

(21) Appl. No.: 13/292,114

(22) Filed: Nov. 9, 2011

(65) Prior Publication Data

US 2012/0130191 A1 May 24, 2012

Related U.S. Application Data

(60) Provisional application No. 61/416,766, filed on Nov. 24, 2010.

(51) Int. Cl.
*A61B 1/32* (2006.01)
*A61B 17/34* (2006.01)
*A61B 17/00* (2006.01)

(52) U.S. Cl.
CPC ......... *A61B 17/3423* (2013.01); *A61B 17/3431* (2013.01); *A61B 2017/00557* (2013.01); *A61B 2017/3443* (2013.01); *A61B 2017/3466* (2013.01); *A61B 2017/3484* (2013.01); *A61B 2017/3492* (2013.01); *A61B 2017/3445* (2013.01)
USPC ...... 600/208; 600/207; 623/23.65; 623/23.67

(58) Field of Classification Search
CPC ............... A61B 2017/3443; A61B 2017/3445; A61B 2017/3466; A61B 2017/3484; A61B 2017/3492; A61B 2017/3433; A61B 2017/3429; A61B 17/3431; A61B 17/3462; A61B 17/3423; A61B 17/3417
USPC ................. 604/93.01, 164.01, 164.09, 164.1, 604/165.01, 165.03, 167.01, 167.03, 604/167.04, 167.05, 264; 600/200–208, 600/215, 218, 235–238, 37, 184; 606/213, 606/108, 190, 1, 198
See application file for complete search history.

(56) References Cited

U.S. PATENT DOCUMENTS

| 5,232,451 | A | | 8/1993 | Freitas et al. |
| 5,366,478 | A | * | 11/1994 | Brinkerhoff et al. ......... 606/213 |
| 5,425,357 | A | | 6/1995 | Moll et al. |
| 5,634,937 | A | | 6/1997 | Mollenauer et al. |
| 5,803,921 | A | | 9/1998 | Bonadio |
| 5,871,474 | A | | 2/1999 | Hermann et al. |
| 5,906,577 | A | | 5/1999 | Beane et al. |
| 5,990,382 | A | * | 11/1999 | Fox ............................ 623/16.11 |

(Continued)

FOREIGN PATENT DOCUMENTS

| EP | 2 044 889 A1 | 4/2009 |
| EP | 2 289 438 A1 | 3/2011 |
| WO | WO 00/54675 A1 | 9/2000 |

OTHER PUBLICATIONS

European Search Report dated Apr. 19, 2012 for EP 12 15 2164.

*Primary Examiner* — Todd Manahan
*Assistant Examiner* — Marcela I Shirsat

(57) ABSTRACT

An access assembly is provided. The access assembly includes a tubular member having a proximal end and a distal end, the tubular member including a threading extending at least a portion of an internal length of the tubular member. The access assembly further includes a first ring secured at the proximal end of the tubular member and a second ring secured at the distal end of the tubular member. The first ring and the second ring are expandable rings.

20 Claims, 7 Drawing Sheets

(56) References Cited

U.S. PATENT DOCUMENTS

| | | | |
|---|---|---|---|
| 5,993,485 A * | 11/1999 | Beckers | 623/23.65 |
| 5,997,515 A | 12/1999 | de la Torre et al. | |
| 6,033,428 A * | 3/2000 | Sardella | 606/213 |
| 6,099,506 A | 8/2000 | Macoviak et al. | |
| 6,440,063 B1 | 8/2002 | Beane et al. | |
| 6,638,265 B1 | 10/2003 | Ternamian | |
| 6,669,674 B1 | 12/2003 | Macoviak et al. | |
| 7,090,688 B2 | 8/2006 | Nishtala et al. | |
| 7,850,600 B1 | 12/2010 | Piskun | |
| 8,550,992 B2 * | 10/2013 | Kleyman | 600/208 |
| 2005/0165432 A1 | 7/2005 | Heinrich | |
| 2007/0225650 A1 | 9/2007 | Hart et al. | |
| 2008/0081951 A1 | 4/2008 | Frasier et al. | |
| 2008/0086165 A1 | 4/2008 | Lyon et al. | |
| 2009/0093752 A1 * | 4/2009 | Richard et al. | 604/24 |
| 2009/0204158 A1 | 8/2009 | Sweeney | |
| 2009/0221966 A1 | 9/2009 | Richard | |
| 2009/0326332 A1 * | 12/2009 | Carter | 600/235 |
| 2010/0063362 A1 | 3/2010 | Bonadio et al. | |
| 2010/0249526 A1 * | 9/2010 | Shelton et al. | 600/208 |
| 2010/0262080 A1 * | 10/2010 | Shelton et al. | 604/164.09 |

* cited by examiner

EXPANDABLE ACCESS ASSEMBLY INCLUDING AN INTERNAL THREAD MECHANISM

CROSS REFERENCE TO RELATED APPLICATION

The present application claims the benefit of and priority to U.S. Provisional Application Ser. No. 61/416,766 filed on Nov. 24, 2010, the entire contents of which are incorporated herein by reference.

BACKGROUND

1. Technical Field

The present disclosure relates to an apparatus and method for accessing a body cavity. More particularly, the present disclosure relates to an expandable access assembly including an internal thread mechanism for accessing the body cavity.

2. Background of Related Art

Access assemblies configured for reception through an incision into an abdominal cavity are known, as are methods of inserting the access assemblies therethrough. Traditional access assemblies include a rigid cannula that is received through the tissue of the body wall into the body cavity. Endoscopic, laparoscopic and other suitable instruments may then be directed through a housing on the proximal end of the cannula to access the body cavity in a sealing manner.

Compressible assemblies configured for accessing a body cavity and permitting reception of instruments therethrough in a sealing manner are also known. Such compressible assemblies are composed of silicone, thermoplastic elastomers (TPE), rubber, foam, gel and other compressible materials and are configured to be compressed to facilitate insertion into an incision. Typically, such assemblies are deformed by a surgeon using his/her fingers or with the assistance of a grasping device, i.e., forceps. Compression of the assembly reduces the profile of the assembly, thereby facilitating reception of the assembly into the incision. Upon release of the compressive force, the compressed assembly returns to an uncompressed configuration. In the uncompressed configuration, the access assembly seals the incision into the body cavity. The assembly may have one or more access ports for receiving instruments therethrough and may optionally be configured for connection with a source of insufflation gas.

Excessive handling of the compressible access assemblies during placement of the assembly through an incision may compromise or otherwise negatively affect the integrity of the assembly. For example, any coating on the assembly may be rubbed off during handling, or excessive force, oversized/undersized fingers and/or sharp grasping instruments may tear the material comprising the assembly.

Therefore, it would be beneficial to have an access assembly configured to be inserted through tissue without excessive handling and/or without the need for an insertion device.

SUMMARY

Accordingly, an access assembly is provided. The access assembly includes a tubular member having a proximal end and a distal end, the tubular member including a threading extending at least a portion of an internal length of the tubular member. The access assembly further includes a first ring secured at the proximal end of the tubular member and a second ring secured at the distal end of the tubular member. The first ring and the second ring are expandable rings.

The first ring is configured to be received external of the tissue, whereas the second ring is configured to be received within a body cavity.

The tubular member is configured to be tapered in a first configuration to facilitate insertion through the tissue and is configured to define a substantially hour-glass shape in a second configuration. The tubular member is further configured to receive a threaded plug that cooperates with the threading extending at least a portion of the internal length of the tubular member. Additionally, the tubular member may include a plurality of lumens, each including internal threading extending at least a portion of an internal length of each of the plurality of lumens.

The first ring and the second ring are configured for operable connection with a fluid source. In one embodiment, the first ring and the second ring expand to substantially equal sizes. In another embodiment, the first ring expands to a first size and the second ring expands to a second size, the first size being larger than the second size. In yet another embodiment, the first ring is expanded whereas the second ring is contracted during a surgical operation. In yet another embodiment, the first ring is contracted whereas the second ring is expanded during a surgical operation.

Also provided is a method of accessing a body cavity. The method includes the step of providing a tubular member having a proximal end and a distal end, the tubular member including a threading extending at least a portion of an internal length of the tubular member. The method also includes the step of providing a first ring secured at the proximal end of the tubular member and a second ring secured at the distal end of the tubular member. The method further includes the step of expanding the first ring and the second ring.

Also provided is a method of accessing a body cavity. The method includes the steps of providing a tubular member, a first ring, and a second ring, the tubular member being configured to be tapered in a first configuration to facilitate insertion through tissue and being configured to define a substantially hour-glass shape in a second configuration; inserting the tapered access assembly through tissue; adjusting the access assembly in the second configuration; expanding the first ring and the second ring and inserting a threaded plug through the tubular member such that the threaded plug is received by a threading extending at least a portion of an internal length of the tubular member.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
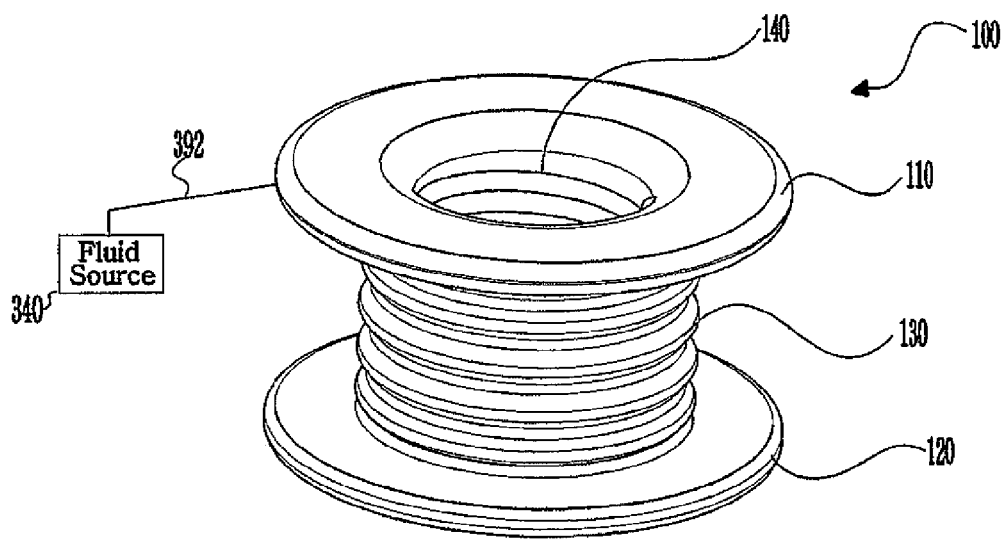
FIG. 1 is a perspective view of an access assembly according to an aspect of the present disclosure, in a first or unexpanded configuration.

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user. While the use of the access assembly is often described herein as engaging an incision, it should be recognized that this is merely exemplary and is not intended to limit the use of the assembly in any way, but rather it should be recognized that the present disclosure is intended to be useable in all instances in situations in which the access assembly engages an incision, a naturally occurring orifice, or any other suitable opening.

Referring initially to FIG. 1, an assembly for access a body cavity is shown generally as access assembly 100. In a first or contracted configuration (FIG. 1), access assembly 100 is configured to be inserted through an incision or other opening in tissue without excessive handling or manipulation of assembly 100 and without a separate insertion device.

Access assembly 100 includes a first ring 110 (or top ring) and a second ring 120 (or bottom ring). A tubular member 130 having a proximal end and a distal end is positioned between the first ring 110 and the second ring 120. The first ring 110 is secured at the proximal end of the tubular member 130, whereas the second ring 120 is secured at the distal end of the tubular member 130. Access assembly 100 includes a cavity or opening 140 for receiving a threaded plug, as described below with reference to FIG. 3. In FIG. 1, the first ring 110, the second ring 120, and the tubular member 130 are shown in an unexpanded or contracted configuration. Additionally, a fluid source 390 is shown in FIG. 1 connected to the first ring 110 via tubing 392 (explained below with reference to FIG. 3).

Figure 2:
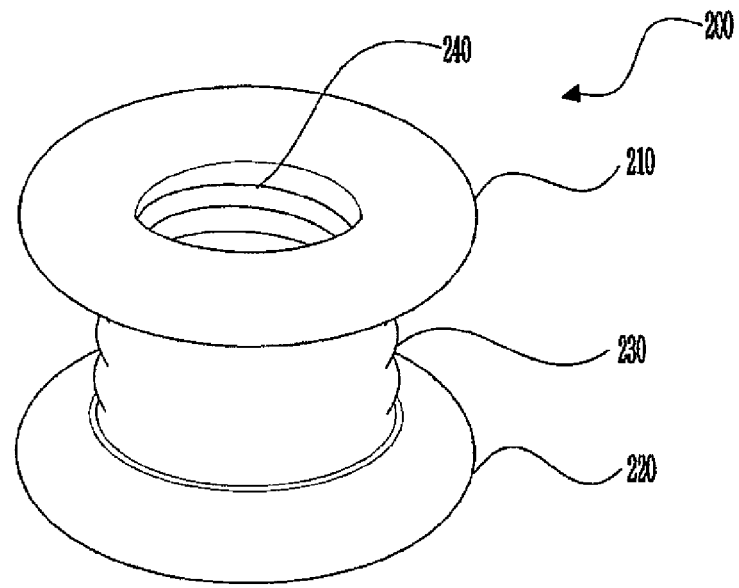
FIG. 2 is a perspective view of the access assembly of FIG. 1 according to an aspect of the present disclosure, in a second or expanded configuration.

Referring to FIG. 2, in a second or expanded configuration, access assembly 200 is configured to selectively seal an opening through tissue into a body cavity.

Access assembly 200 includes a first ring 210 (or top ring) and a second ring 220 (or bottom ring). A tubular member 230 having a proximal end and a distal end is positioned between the first ring 210 and the second ring 220. The first ring 210 is secured at the proximal end of the tubular member 230, whereas the second ring 220 is secured at the distal end of the tubular member 230. Access assembly 200 includes a cavity or opening 240 for receiving a threaded plug, as described below with reference to FIG. 4. In FIG. 2, the first ring 210, the second ring 220, and the tubular member 230 are shown in an expanded configuration. The first ring 210, the second ring 220, and the tubular member 230 may be expanded via a fluid source described below with reference to FIGS. 3 and 4. Therefore, access assemblies 100, 200 are configured for operable connection to a fluid source, such as $CO_2$, saline, etc. (FIGS. 3 and 4) such that the access assemblies 100, 200 may be expanded or inflated.

Access assembly 100 may be maintained in the tapered or first configuration by using a temporary adhesive, a dissolvable coating, a tear-away sleeve or any other suitable means. In an alternate embodiment, a shrink-wrap sleeve or tube may be used to achieve the tapered configuration of access assembly 100. As will be described in further detail below, either upon receipt within an opening formed in tissue or upon the start of expansion of access assembly 100 into access assembly 200, the adhesive, coating, sleeve or other material maintaining the tapered or first configuration dissolves, tears or otherwise releases access assembly 100 from the tapered or first configuration, thereby permitting expansion into access assembly 200.

It is envisioned that access assembly 100 may be provided to a surgeon in the first configuration or access assembly 200 may be provided to a surgeon in the second configuration for commencing surgery. Thus, the surgeon has a choice of either inserting an expanded or unexpanded access assembly.

Figure 3:
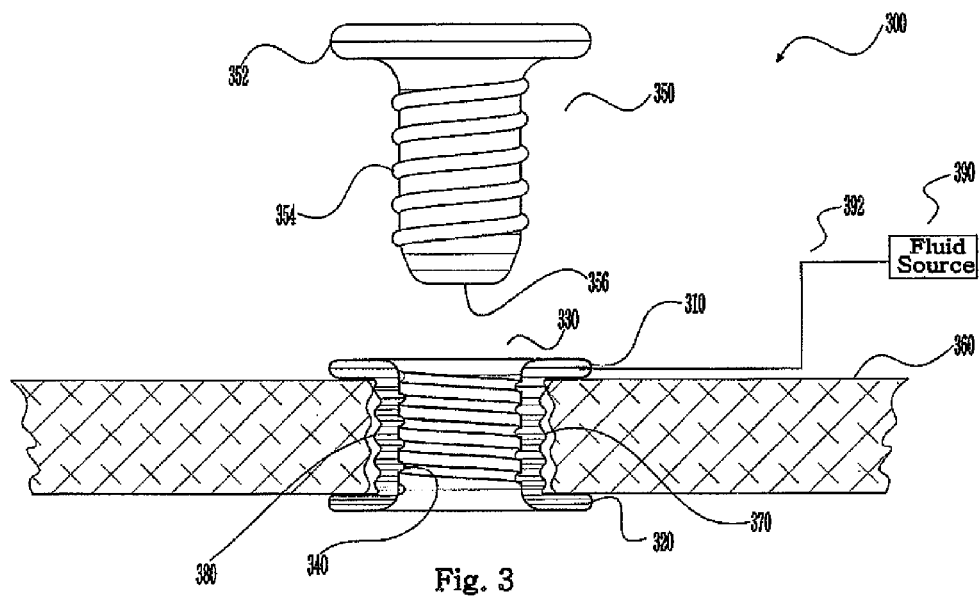
FIG. 3 is a cross-sectional view of the access assembly of FIG. 1, according to an aspect of the present disclosure, inserted into tissue in an unexpanded configuration.

With reference to FIG. 3, a cross-sectional view 300 of the access assembly of FIG. 1, according to an aspect of the present disclosure, inserted into tissue in a contracted configuration is presented.

In FIG. 3, access assembly 100 of FIG. 1 is inserted into tissue 360. The cross-sectional view 300 depicts the access assembly 100 in an expanded configuration. Access assembly 100 includes a first ring 310 (or top ring) and a second ring 320 (or bottom ring). Tubular member portions 370, 380 having proximal ends and distal ends are positioned between the first ring 310 and the second ring 320. The first ring 310 is secured at the proximal end of the tubular member 330, whereas the second ring 320 is secured at the distal end of the tubular member 330. The access assembly 100 includes internal threading 340.

A threaded plug 350 includes a head portion 352, threads 354, and a distal end 356. The threaded plug 350 is configured to be inserted into the access assembly 100. The threads 354 of the threaded plug 350 are configured to cooperate with the internal threading 340 of the access assembly 100. The threaded plug 350 allows the physician to selectively close the opening to reduce loss of fluid, minimizing contamination, etc. It is contemplated that the threaded plug 350 includes one or more lumens for receiving instruments.

Additionally, the first ring 310 and/or the second ring 320 and/or the tubular member portions 370, 380 may be connected to a fluid source 390 via tubing 392. A plurality of different fluid sources may be contemplated by one skilled in the art.

Figure 4:
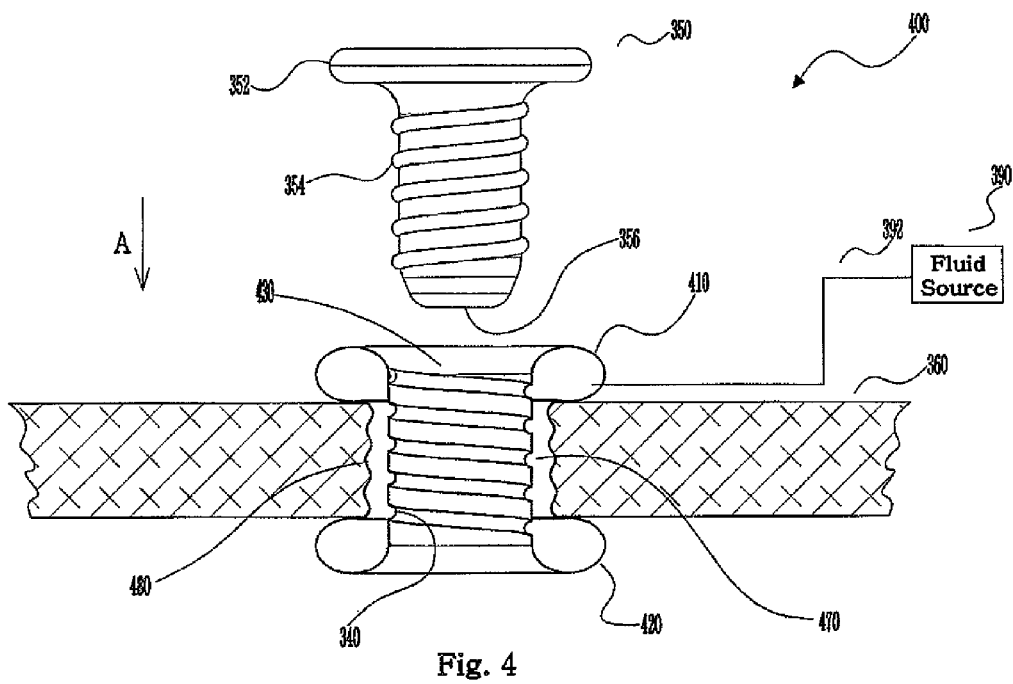
FIG. 4 is a cross-sectional view of the access assembly of FIG. 2, according to an aspect of the present disclosure, where the access assembly is expanded after inserted into tissue.

With reference to FIG. 4, a cross-sectional view of the access assembly of FIG. 2, according to an aspect of the present disclosure, where the access assembly is expanded while inserted into tissue is presented.

In FIG. 4, access assembly 200 of FIG. 2 has been inserted into tissue 360. The cross-sectional view 400 depicts the access assembly 200 in an expanded configuration. Access assembly 200 includes a first ring 410 (or top ring) and a second ring 420 (or bottom ring). Tubular member portions 470, 480 having proximal ends and distal ends are positioned between the first ring 410 and the second ring 420. The first ring 410 is secured at the proximal end of the tubular member 430, whereas the second ring 420 is secured at the distal end of the tubular member 430. The access assembly 200 includes internal threading 340.

A threaded plug 350 includes a head portion 352, threads 354, and a distal end 356. The threaded plug 350 is configured to be inserted into the access assembly 200. The threads 354 of the threaded plug 350 are configured to cooperate with the internal threading 340 of the access assembly 200. Arrow "A" indicates the direction of insertion of the threaded plug 350 into or through the access assembly 200. The threaded plug 350 allows the physician to selectively close the opening to reduce loss of fluid, minimizing contamination, etc. It is contemplated that the threaded plug 350 includes one or more lumens for receiving instruments.

Additionally, the first ring 410 and/or the second ring 420 and/or the tubular member portions 470, 480 may be connected to the fluid source 390 via tubing 392. A plurality of different fluid sources may be contemplated by one skilled in the art.

Expandable access assembly 410 may be constructed of plastic, polymer, fabric or other suitable material. Expandable access assembly 410 may be molded, extruded, sewn or formed in any other suitable manner. In one embodiment, the first ring 410 and the second ring 420 may be securely affixed to tubular member portions 470, 480 by adhesive, bonding, welding or other suitable means. In an alternative embodiment, the first ring 410 and the second ring 420 may be configured for selective engagement with tubular member portions 470, 480.

In an alternative embodiment, access assemblies 100, 200 may include a plurality of openings. For example, the tubular member 130, 230 may include a plurality of lumens, each lumen including internal threading 340 extending at least a portion of an internal length of the tubular members 130, 230 (see FIGS. 1 and 2). Moreover, although shown including a centrally located opening, it is envisioned that the arrangement of access assemblies 100, 200 and the one or more plurality of lumens may be modified to better suit an application or procedure. For example, at least one lumen of the plurality of lumens may be configured to directly seal one or more instruments inserted therethrough. Alternatively, each of the plurality of lumens may include one or more valve members (not shown) for receiving an instrument therethrough in a sealing manner. Additionally, the one or more valve members may seal each of the plurality of lumens in the absence of an instrument received therethrough.

Figure 5:
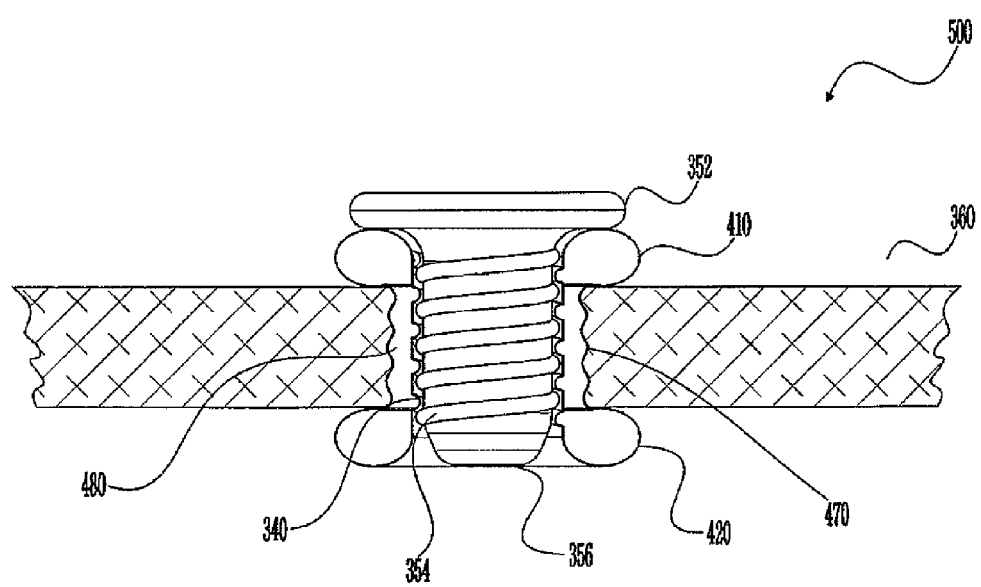
FIG. 5 is a cross-section view of the access assembly of FIG. 1, according to an aspect of the present disclosure, where a threaded plug is inserted through the access assembly.

With reference to FIG. 5, a cross-section view 500 of the access assembly of FIG. 1, according to an aspect of the present disclosure, where a threaded plug is inserted through the access assembly is presented.

In FIG. 5, threaded plug 350 (see FIG. 4) has been inserted into access assembly 200 (see FIG. 2). In the expanded configuration, access assembly 200 creates a seal within an opening to prevent the escape of insufflation gas therethrough. Expandable access assembly 200 may be expanded with any suitable fluid, including an insufflation gas or water. Expandable access assembly 200 may define a substantially hourglass shape when viewed from the side. First ring 410 and second ring 420 aid in minimizing movement of the expandable access assembly 200 longitudinally through an opening. Tubular member portions 470, 480 are of a length sufficient that the first ring 410 is maintained external the body while the second ring 420 is received within the abdominal cavity. Thus, the threaded plug 350 is configured to be inserted into the access assembly 100 or 200. The threads 354 of the threaded plug 350 are configured to cooperate with the internal threading 340 of the access assembly 100 to enable a fluid-tight seal. The distal end 356 of the threaded plug 250 rests on the second ring 420, whereas the head 352 of the threaded plug 350 rests on the first ring 410.

Figure 6A:
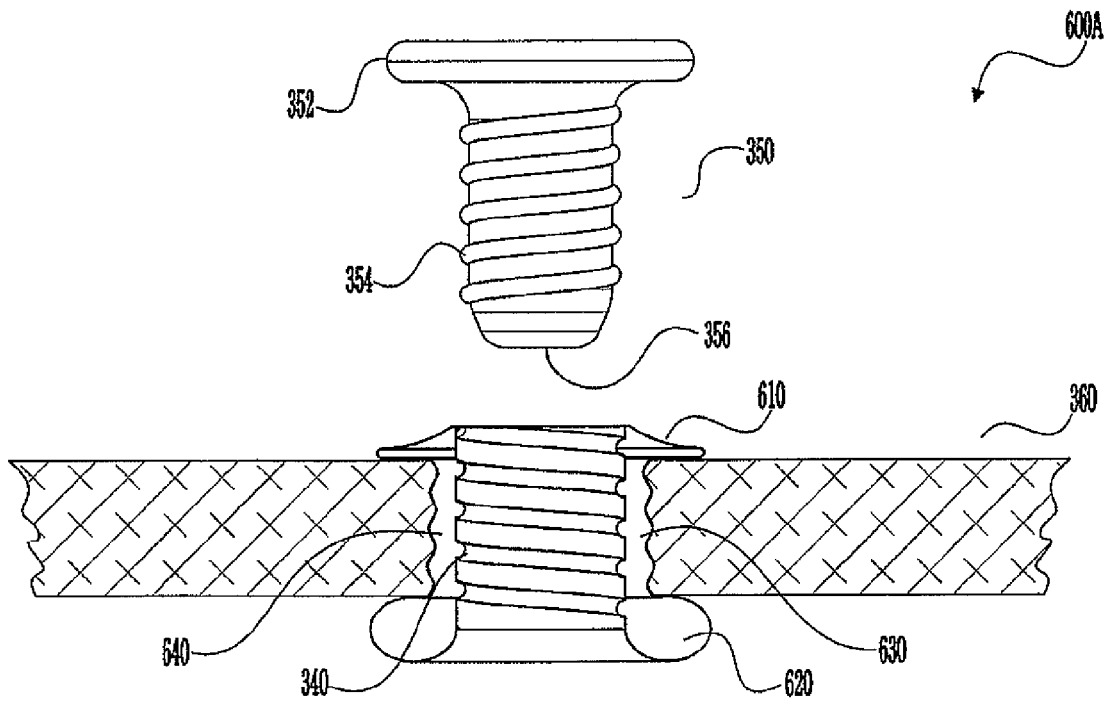
FIG. 6A is a cross-sectional view of an access assembly, according to a second aspect of the present disclosure, where a bottom ring of the access assembly is expandable.
Figure 6B:
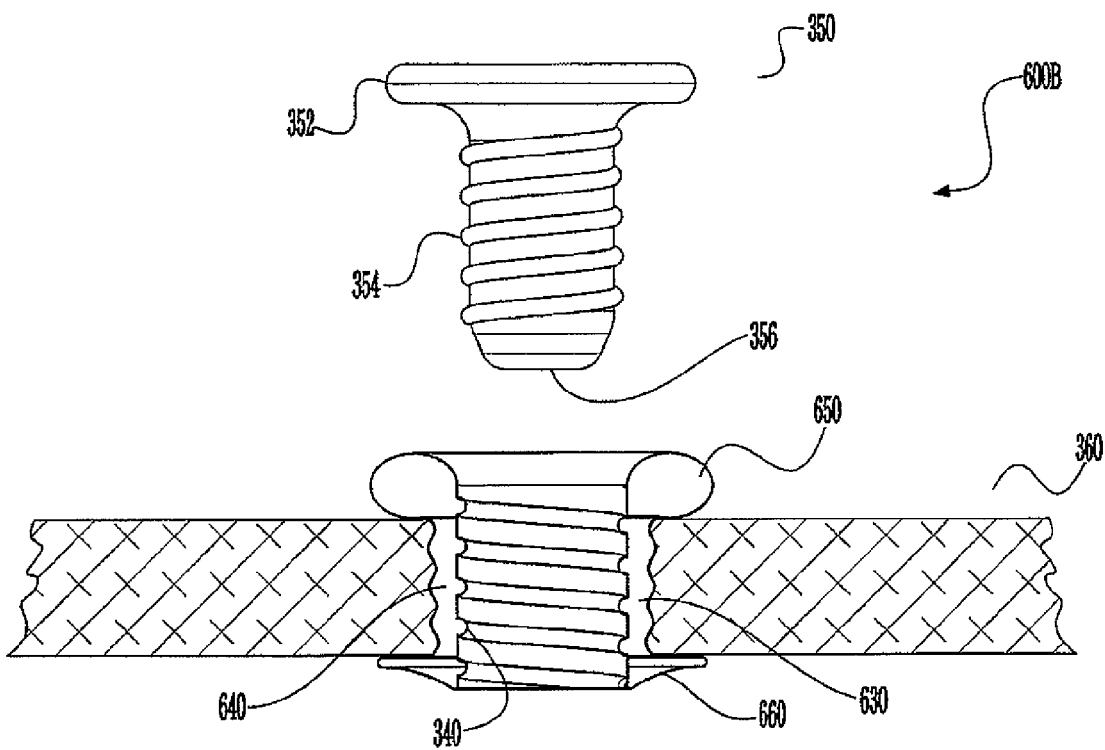
FIG. 6B is a cross-sectional view of an access assembly, according to a second aspect of the present disclosure, where a top ring of the access assembly is expandable.

Referring to FIG. 6A, a cross-sectional view 600A of an access assembly, according to a second aspect of the present disclosure, where a bottom ring of the access assembly is expandable is presented. Referring to FIG. 6B, a cross-sectional view 600B of an access assembly, according to a second aspect of the present disclosure, where a top ring of the access assembly is expandable is presented.

In FIG. 6A, the first ring 610 is unexpanded, whereas the second ring 620 is expanded. The tubular member portions 630, 640 are expanded. However, such portions may be unexpanded too. In FIG. 6B, the first ring 650 is expanded, whereas the second ring 660 is unexpanded. The tubular member portions 630, 640 are expanded. However, such portions may be unexpanded too.

In operation, a surgeon is provided with the capability to selectively expand either the first ring or the second ring. The surgeon may determine that a tighter seal is necessary on the top portion of the tissue or that a tighter seal is necessary on the bottom portion of the tissue. As such, he/she may selectively expand/contract either portion at will as shown in FIGS. 6A and 6B.

Figure 7A:
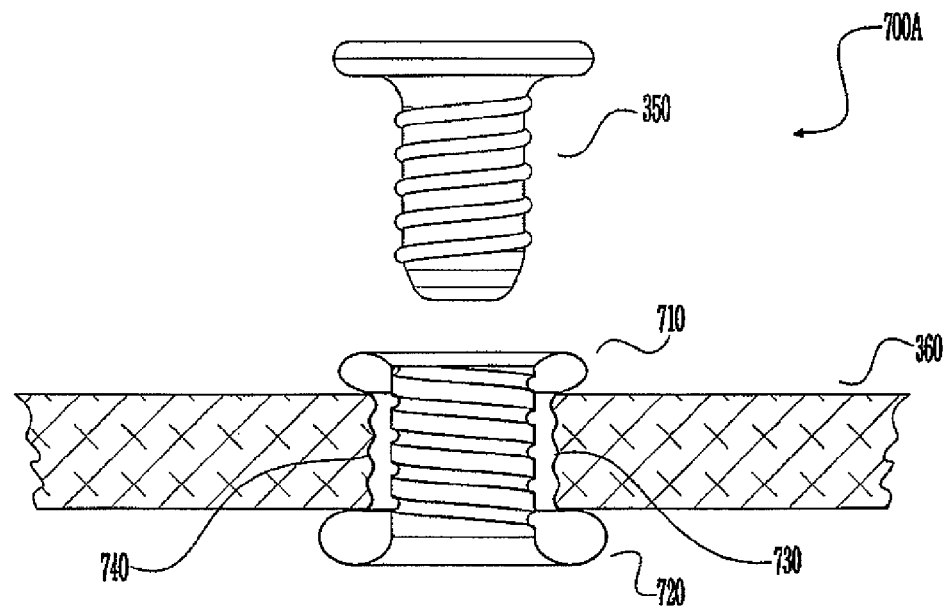
FIG. 7A is a cross-sectional view of an access assembly, according to a third aspect of the present disclosure, where a bottom ring of the access assembly is expanded to a first size and a top ring of the access assembly is expanded to a second size, the first size being larger than the second size.
Figure 7B:
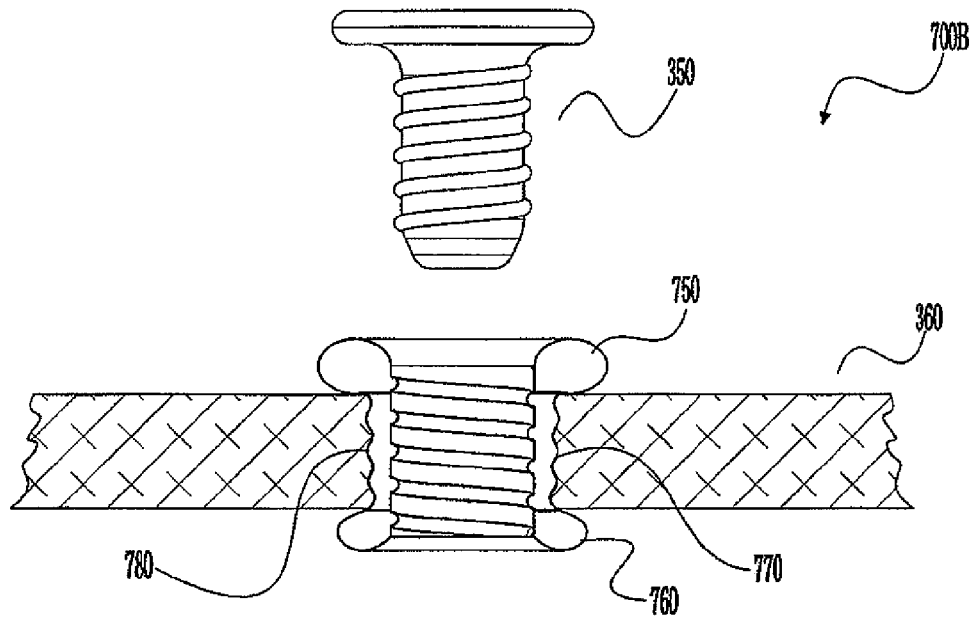
FIG. 7B is a cross-sectional view of an access assembly, according to a third aspect of the present disclosure, where a bottom ring of the access assembly is expanded to a first size and a top ring of the access assembly is expanded to a second size, the second size being larger than the first size.

Referring to FIG. 7A, a cross-sectional view 700A of an access assembly, according to a third aspect of the present disclosure, where a bottom ring of the access assembly is expanded to a first size and a top ring of the access assembly is expanded to a second size, the first size being larger than the second size. Referring to FIG. 7B, a cross-sectional view 700B of an access assembly, according to a third aspect of the present disclosure, where a bottom ring of the access assembly is expanded to a first size and a top ring of the access assembly is expanded to a second size, the second size being larger than the first size is presented.

In an alternative embodiment, in FIG. 7A, the first ring 710 is expanded to a first size, whereas the second ring 720 is expanded to a second size, the second size being larger than the first size. The tubular member portions 730, 740 may be expanded to the first size, to the second size or to a third size being different than the first and second sizes. In other words, a surgeon may determine that different seal pressure is necessary for the top and bottom portions of the access assembly once inserted through tissue 360. As such, the surgeon has the capability to selectively expand/contract the rings 710, 720 and tubular member portions 730, 740 to any desired levels in order to enable proper cooperation between the threaded plug 350 and the internal threads 340 (see FIG. 5).

In an alternative embodiment, in FIG. 7B, the first ring 750 is expanded to a first size, whereas the second ring 760 is expanded to a second size, the first size being larger than the second size. The tubular member portions 770, 780 may be expanded to the first size, to the second size or to a third size being different than the first and second sizes. In other words, a surgeon may determine that different seal pressure is necessary for the top and bottom portions of the access assembly once inserted through tissue 360. As such, the surgeon has the capability to selectively expand/contract the rings 750, 760 and tubular member portions 770, 780 to any desired levels in order to enable proper cooperation between the threaded plug 350 and the internal threads 340 (see FIG. 5).

Figure 8:
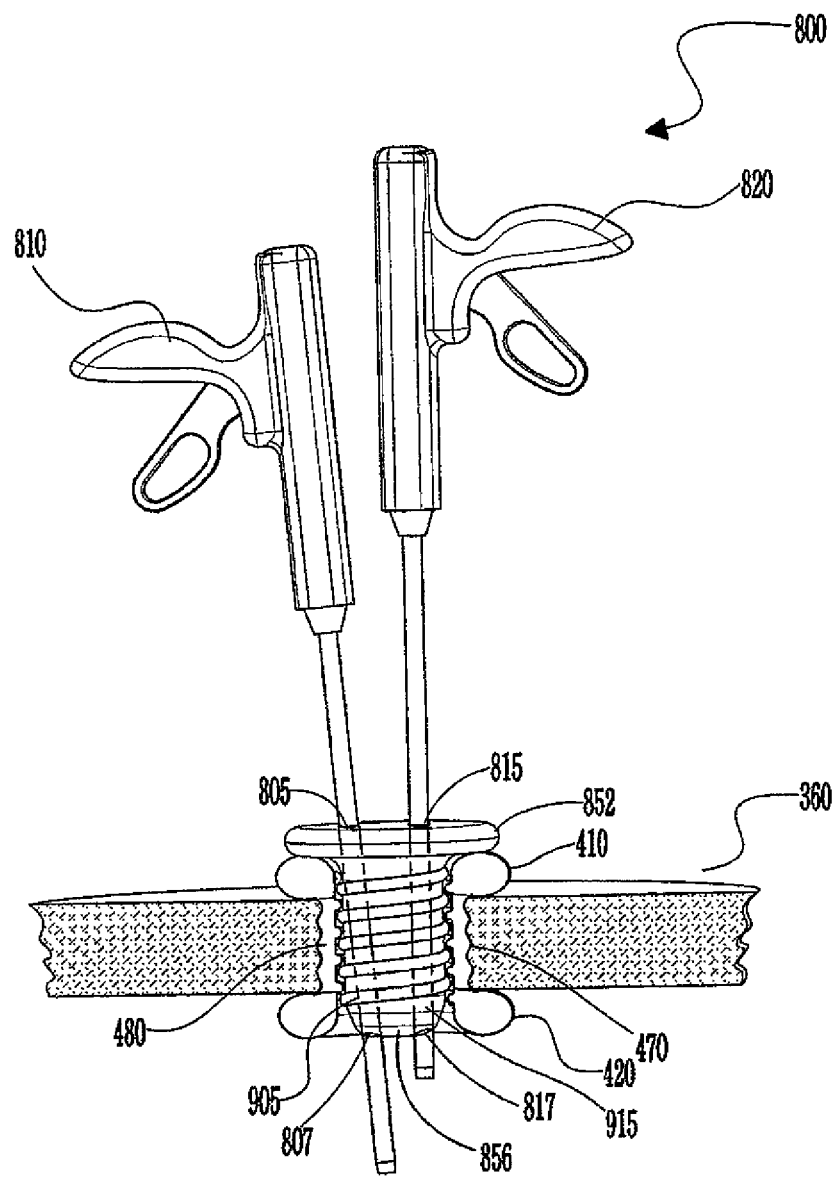
FIG. 8 is a perspective view of an access assembly having a threaded plug inserted therethrough, where the threaded plug includes a plurality of lumens or channels for receiving a plurality of surgical instruments therethrough, in accordance with the present disclosure.

With reference to FIG. 8, a perspective view 800 of an access assembly having a threaded plug 900 (see FIGS. 9A, 9B) inserted therethrough is presented, where the threaded plug 900 includes a plurality of lumens or channels 905, 915 for receiving a plurality of surgical instruments 810, 820 therethrough, in accordance with the present disclosure.

In FIG. 8, the threaded plug 900 has been inserted through an access assembly, as described hereinabove. In the expanded configuration, the access assembly creates a seal within an opening to prevent the escape of insufflation gases. The head 852 of the threaded plug 900 may include a plurality of openings 805, 815. One skilled in the art may contemplate a plurality of different openings of different shapes and sizes. Additionally, the distal end 856 of the threaded plug 900 may include a plurality of openings 807, 817 for permitting the exit of the distal ends of the surgical instruments 810, 820 inserted through the threaded plug 900. Opening 807 may correspond to opening 805, whereas opening 817 may correspond to opening 815. As such, lumens or channels 905, 915 may be formed, extending through the entire length of the threaded plug 900, as described below with reference to FIGS. 9A and 9B. In other words, lumen 905 includes opening 805 at its proximal end and opening 807 at its distal end, whereas lumen 915 includes opening 815 at its proximal end and opening 817 at its distal end.

Figure 9A:
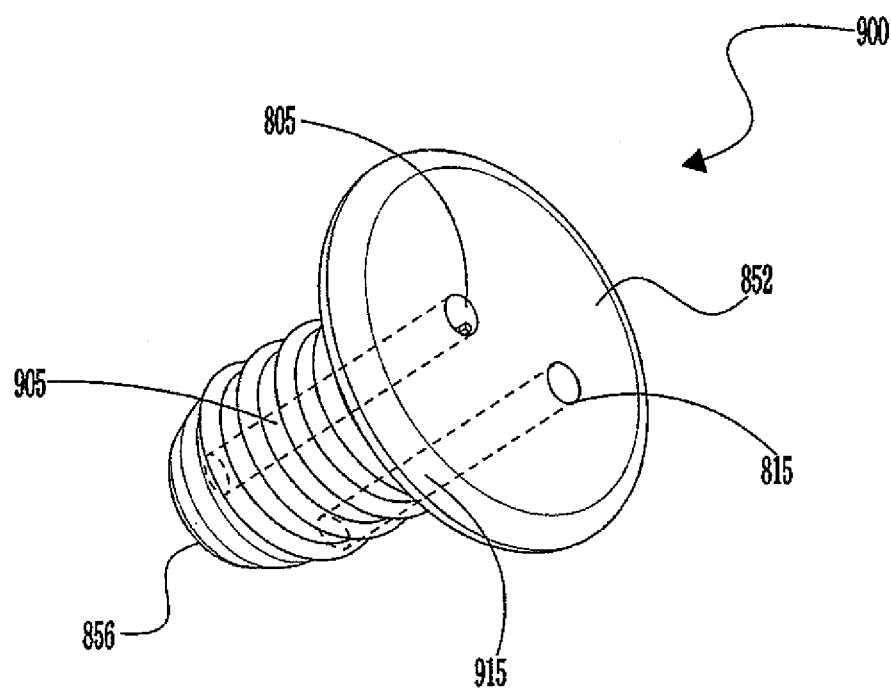
FIGS. 9A and 9B are perspective top and bottom views of the threaded plug of FIG. 8, respectively, where the top and bottom portions of the plurality of lumens or channels are illustrated, in accordance with the present disclosure.
Figure 9B:
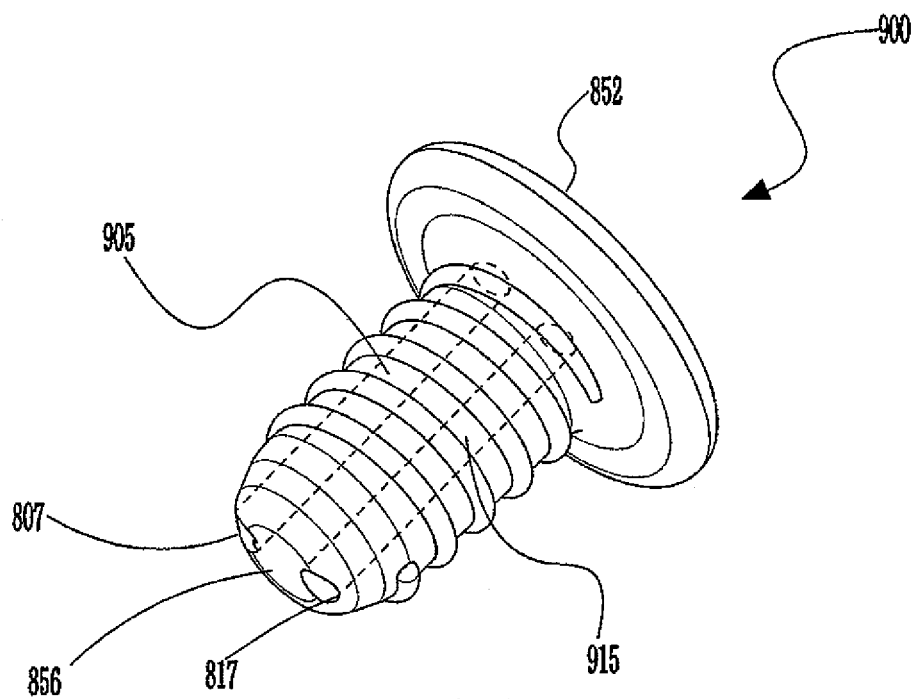

With reference to FIGS. 9A and 9B, perspective top and bottom views of the threaded plug 900 of FIG. 8, respectively, are presented, where the top and bottom portions of the plurality of lumens or channels 905, 915 are illustrated, in accordance with the present disclosure.

For example, FIG. 9A depicts openings 805, 815 of the head 852 of the threaded plug 900, whereas FIG. 9B depicts openings 807, 817 of the distal end 856 of the threaded plug 900. As shown, lumens or channels 905, 915 extend the entire length of the threaded plug 900, such that surgical instruments 810, 820 (see FIG. 8) are inserted through the threaded plug 900 in order for the distal ends of such surgical instruments 810, 820 to be exposed within the cavity of patient. One skilled in the art may contemplate any type of angular disposition for the lumens or channels 905, 915. For example, the lumens or channels 905, 915 may extend straight through the threaded plug 900. However, the lumens or channels 905, 915 may angularly extend through the threaded plug 900. For instance, the angular displacement may be 5° degrees, 10° degrees, 15° degrees, 20° degrees or any other angular displacement contemplated by one skilled in the art. Of course, the lumens or channels 905, 915 may be formed in order to receive any type of surgical instruments, such as cannulas, trocars, illuminating devices, cameras, etc. One skilled in the art may contemplate inserting any types of objects through the channels or lumens 905, 915 that aid a surgeon in performing a surgery.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. An access assembly configured and dimensioned for positioning within an opening in tissue, the access assembly comprising:
   a tubular member having a proximal end and a distal end, the tubular member including an inner wall defining a passageway extending through the tubular member, the inner wall including internal threading;
   a first ring secured at the proximal end of the tubular member;
   a second ring secured at the distal end of the tubular member;
   wherein the first ring, the second ring, and the tubular member are inflatable; and
   a plug configured for insertion into the passageway of the tubular member, the plug including external threading configured and dimensioned for engagement with the internal threading to selectively secure the plug within the passageway to inhibit fluid communication through the passageway of the tubular member and to prevent surgical instruments from passing through the passageway of the tubular member.

2. The access assembly according to claim 1, wherein the first ring is configured to be received external of the tissue and wherein the second ring is configured to be received within a body cavity.

3. The access assembly according to claim 1, wherein the tubular member is configured to be tapered in a first configuration to facilitate insertion through the tissue and is configured to define a substantially hour-glass shape in a second configuration.

4. The access assembly according to claim 1, wherein the tubular member is independently inflatable with respect to at least one of the first ring and the second ring.

5. The access assembly according to claim 1, wherein the first ring and the second ring are configured for operable connection with a fluid source.

6. The access assembly according to claim 1, wherein the first ring and the second ring inflate to substantially equal sizes.

7. The access assembly according to claim 1, wherein the first ring inflates to a first size and the second ring inflates to a second size, the first size being larger than the second size.

8. The access assembly according to claim 1, wherein the first ring is expanded whereas the second ring is contracted during a surgical operation.

9. The access assembly according to claim 1, wherein the second ring is expanded whereas the first ring is contracted during a surgical operation.

10. The access assembly according to claim 1, wherein a distal surface of the first ring is longitudinally fixed from movement with regard to a proximal surface of the second ring.

11. The access assembly according to claim 1, wherein the passageway defines a longitudinal axis, wherein a first plane is defined perpendicularly to the longitudinal axis, and wherein at least a portion of the internal threading of the tubular member and at least a portion of the first ring are within the first plane.

12. The access assembly according to claim 11, wherein a second plane is defined perpendicularly to the longitudinal axis, and wherein at least a portion of the internal threading of the tubular member and at least a portion of the second ring are within the second plane.

13. A method of accessing a body cavity, the method comprising:
   inserting an access assembly including a tubular member having a first ring secured to a proximal end of the tubular member and a second ring secured to a distal end of the tubular member into an opening in tissue;
   inflating the first ring, the second ring, and the tubular member;
   inserting a plug into an internal passageway extending through the tubular member to prevent surgical instruments from passing through the internal passageway of the tubular member; and
   rotating the plug in relation to the tubular member to cause external threading provided on the plug to engage internal threading provided within the internal passageway to selectively secure the plug within the internal passageway to inhibit fluid communication through the internal passageway of the tubular member.

14. The method according to claim 13, further comprising creating the opening in the tissue.

15. The method according to claim 13, further comprising operably connecting the first ring and the second ring with a fluid source.

16. The method according to claim 13, further comprising inflating the first ring and the second ring to substantially equal sizes.

17. The method according to claim 13, further comprising inflating the first ring to a first size and the second ring to a second size, the first size being different than the second size.

18. The method according to claim 13, further comprising expanding the first ring and contracting the second ring when accessing the body cavity.

19. The method according to claim 13, further comprising expanding the second ring and contracting the first ring when accessing the body cavity.

20. A method of accessing a body cavity, the method comprising:
   inserting an access assembly including a tubular member having a first ring and a second ring into an opening in tissue while the access assembly is in a first, tapered configuration;
   inflating the first ring, the second ring, and the tubular member to move the access assembly into a second configuration in which the access assembly defines an hour-glass shape;
   inserting a plug into an internal passageway extending through the tubular member to prevent surgical instruments from passing through the internal passageway of the tubular member; and
   rotating the plug in relation to the tubular member to cause external threading provided on the plug to engage internal threading provided within the internal passageway to selectively secure the plug within the internal passageway to inhibit fluid communication through the internal passageway of the tubular member.

* * * * *